(12) United States Patent
Asano et al.

(10) Patent No.: US 7,776,570 B2
(45) Date of Patent: Aug. 17, 2010

(54) L-AMINO ACID AMIDE ASYMMETRIC HYDROLASE AND DNA ENCODING THE SAME

(75) Inventors: Yasuhisa Asano, Toyama (JP); Atsushi Inoue, Niigata (JP)

(73) Assignee: Mitsubishi Gas Chemical Company, Inc., Chiyoda-ku, Tokyo (JP)

(*) Notice: Subject to any disclaimer, the term of this patent is extended or adjusted under 35 U.S.C. 154(b) by 251 days.

(21) Appl. No.: 12/174,995

(22) Filed: Jul. 17, 2008

(65) Prior Publication Data

US 2010/0009415 A1 Jan. 14, 2010

Related U.S. Application Data

(62) Division of application No. 11/658,063, filed as application No. PCT/JP2005/009345 on May 23, 2005, now Pat. No. 7,432,086.

(30) Foreign Application Priority Data

Jul. 22, 2004 (JP) .............................. 2004-214241

(51) Int. Cl.
- C12P 13/04 (2006.01)
- C12N 9/78 (2006.01)
- C12N 9/80 (2006.01)
- C07H 21/04 (2006.01)

(52) U.S. Cl. ...................... 435/106; 435/227; 435/228; 435/252.3; 536/23.2

(58) Field of Classification Search ................. 435/106, 435/252.3, 227, 228; 536/23.2
See application file for complete search history.

(56) References Cited

U.S. PATENT DOCUMENTS

| | | | |
|---|---|---|---|
| 4,918,196 A | 4/1990 | Doya et al. | |
| 5,215,897 A | 6/1993 | Sakashita et al. | |
| 5,985,632 A | 11/1999 | Stelkes-Ritter et al. | |
| 6,617,139 B1 | 9/2003 | Nakamura et al. | |
| 7,070,963 B2 | 7/2006 | Verseck et al. | |
| 2003/0087402 A1 | 5/2003 | Brieden et al. | |
| 2003/0236434 A1 | 12/2003 | Gimi et al. | |

FOREIGN PATENT DOCUMENTS

| | | |
|---|---|---|
| EP | 0 530 522 | 3/1993 |
| JP | 08-256771 | 10/1996 |
| JP | 3112090 | 9/2000 |
| JP | 2002-253256 | 9/2002 |
| JP | 2003-250558 | 9/2003 |
| WO | WO 2004/090152 | 10/2004 |

OTHER PUBLICATIONS

Larimer, et al. *Rhodopseudomans palustris* CGA009 complete genome; segment 8/16. Database GenBank Accession No. BX572600, Apr. 2004. Gene 297643..298632.

Hermes, et al. "Purification and Characterization of an L-Amino Amidase from *Mycobacterium neoaurum* ATCC 25795," *Applied & Environ. Microbiol.*, vol. 60, No. 1, pp. 153-159, 1994.

Inoue, et al. "Asymmetric Synthesis of L-α-Methylcysteine with the Amidase from *Xanthobacter flavus* NR303," *Adv. Synth. Catal.* No. 347, pp. 1132-1138, 2005.

*Primary Examiner*—Tekchand Saidha
(74) *Attorney, Agent, or Firm*—Knobbe, Martens, Olson & Bear, LLP

(57) ABSTRACT

A recombinant microorganism is produced by introducing a DNA encoding an enzyme which hydrolyzes an amido bond of L-amino acid amide, especially L-2-alkylcysteine amide, and L-amino acid is produced by using cells or cell processed product of the obtained microorganism.

14 Claims, No Drawings

L-AMINO ACID AMIDE ASYMMETRIC HYDROLASE AND DNA ENCODING THE SAME

RELATED APPLICATIONS

This application is a divisional of U.S. application Ser. No. 11/658,063, filed Jan. 19, 2007 now U.S. Pat. No. 7,432,086 which is the U.S. National Phase under 35 U.S.C. §371 of International Application PCT/JP2005/009345, filed May 23, 2005, which was published in a language other than English, which claims priority of JP Application No. 2004-214241, filed Jul. 22, 2004.

TECHNICAL FIELD

The present invention relates to a novel L-amino acid amide asymmetric hydrolase and a DNA encoding the same, and use thereof. More specifically, the present invention relates to a novel enzyme having at least an activity of stereoselectively hydrolyzing an amide bond of an L-amino acid amide, particularly L-2-alkylcysteine amide; a DNA encoding the protein of the enzyme; a recombinant microorganism into which the DNA has been introduced; a method of significantly improve the culture productivity of the enzyme by using the recombinant microorganism, and a method of efficiently converting an L-amino acid amide into an L-amino acid by using the obtained enzyme. Optically active amino acids and amino acid amides, particularly optically active 2-alkylcysteine and 2-alkylcysteine amide are important materials serving as production intermediates of various industrial chemicals, pharmaceuticals, and agricultural chemicals.

BACKGROUND ART

As a method of producing an optically active amino acid from an amino acid amide, for example, a method comprising utilizing a microorganism which contains an enzyme stereoselectively hydrolyzing an amide bond of a racemic amino acid amide or cell processed product of such a microorganism is known as an industrially advantageous method (Patent Documents 1 and 2). Such an enzyme, which is a catalyst derived from a living body, has excellent characteristics that it allows a product of interest to be produced with extremely high reaction specificity under a moderate reaction condition. However, a kind of substrate to be catalyzed is limited, and a large amount of cells are required for reaction because of small amount of the enzyme to be produced by cells, and therefore, there is a technical problem that the method cannot be employed because of its economical disadvantage.

Therefore, in order to increase production amount of an enzyme having the above-mentioned activity, it has been attempted to prepare a transformant by cloning a DNA encoding an enzyme protein of an enzyme which stereoselectively hydrolyzes an amino acid amide by a gene recombination technique and then to produce an optically active amino acid from a racemic amino acid amide by using the transformant (Patent Documents 3 to 8 and Non-patent Document 1).

Patent Document 3, for example, discloses D-amidase derived from *Variovorax*, a DNA encoding the D-amidase, a plasmid, a vector and a microorganism each containing such a nucleic acid, a nucleic acid which hybridizes with the nucleic acid, primers for producing the nucleic acid, and the like. Patent Document 4 discloses a modified amino acid amidase and a method of producing D-amino acid using the same. However, these methods work only for D-amino acid amide, so the L-amino acid amides cannot be hydrolyzed by the methods.

On the other hand, as an example of an enzyme which acts on an L-amino acid amide, Patent Document 5 discloses an enzyme which stereoselectively hydrolyzes an amide bond of an L-amino acid amide and is derived from *Pseudomonas azotoformans*, and a DNA encoding the enzyme. The enzyme has a high activity to L-proline amide but has a low activity to other L-amino acid amides.

In addition, Patent Document 6 discloses an enzyme protein derived from *Comamonas acidovorans* and a DNA encoding the protein, and a method of producing an optically active organic acid using the enzyme protein. Patent Document 6 also discloses asymmetric hydrolysis of an amino acid amide in which only leucine amide and phenylalanine amide are used as a substrate. Further, Patent Document 7 discloses a protein having an amidase activity to stereoselectively hydrolyze α-amino acid amide and α-hydroxylic acid amide and a DNA encoding the protein. However, only t-leucine amide is disclosed as a preferable amino acid amide substrate. Furthermore, Patent Document 8 discloses a method of obtaining a microorganism containing a peptide amidase, a microorganism obtained by the method, a peptide amidase contained in the microorganism, and a method of using them. This enzyme has a high activity to dipeptide amide, N-acetyl amino acid amide, and protected amino acid amide, while it has no activity to hydrolyze an unprotected amino acid amide. Still further, Nonpatent Document 1 discloses an enzyme which stereoselectively hydrolyzes an amino acid amide having an alkyl group at position a. However, examples disclosed therein are limited to amino acids having a side chain of hydrocarbon type such as methylvaline, methylleucine, and methylphenylalanine, and there is no description at all about 2-alkylcysteine which has a mercapto group and an alkyl group in side chain.

The 2-alkylcysteine is a derivative of alkylcysteine which is an atypical amino acid other than typical natural amino acids, and has an alkyl group on the carbon atom at position α and multiple reactive substituents including mercapto group, amino group and carboxyl group in its molecule. In particular, optically active form of 2-alkylcysteine is a compound expected to be widely used as a production raw material for various industrial chemicals, pharmaceuticals, agricultural chemicals and the like, or a general chiral building block, and is also extremely useful from the industrial viewpoint, so a production method thereof which is industrially advantageous and inexpensive has been desired to be developed.

However, as described above, there has not been known an enzyme which has an activity to stereoselectively hydrolyze an amide bond in the L-2-alkylcysteine amide, and therefore, there has not been known a method of producing an optically active 2-alkylcysteine or an optically active 2-alkylcysteine amide by using such an enzyme. Further, there have been demands for an L-amino acid amide hydrolase which is highly active and highly stereoselective and has a wide substrate spectrum for other L-amino acid amides so as to be applicable to various amino acid amides useful as industrial raw materials, and methods of efficiently producing and using the enzyme.

Patent Document 1: JP-A-61-293394
Patent Document 2: JP-A-62-55097
Patent Document 3: JP-A-2003-225094
Patent Document 4: JP-A-2002-253256

Patent Document 5: JP-A-2003-250558
Patent Document 6: JP-A-08-256771
Patent Document 7: WO 00/63354
Patent Document 8: Japanese Patent No. 3112090
Non-patent Document 1: H. F. M. Hermes et al., Applied and Environmental Microbiology, Vol. 60, No. 1, p. 153-159, 1994

DISCLOSURE OF THE INVENTION

An object of the present invention is to provide an L-amino acid amide asymmetric hydrolase, a DNA encoding the L-amino acid amide asymmetric hydrolase, a recombinant microorganism into which a recombinant DNA containing the DNA has been introduced, and a method of producing an optically active amino acid, particularly an optically active 2-alkylcysteine by using them, all of which can be preferably used for producing an optically active amino acid, particularly an optically active 2-alkylcysteine, which is an industrially useful compound expected to be widely used as a production intermediate for various industrial chemicals, pharmaceuticals, and agricultural chemicals.

The inventors of the present invention made intensive studies to solve the above-mentioned objects, and as a result, found a microorganism having a high enzymatic activity to stereoselectively hydrolyze an amide bond in an L-amino acid amide, particularly an L-2-alkylcysteine amide, and isolated and purified an enzyme exhibiting the above-mentioned catalytic activity from the obtained microorganism for the first time. Further, the inventors of the present invention separated and obtained a DNA encoding the enzyme for the first time, and succeeded in preparing a recombinant DNA containing the DNA and a recombinant microorganism into which the recombinant DNA has been introduced to be expressed. In addition, by culturing the recombinant microorganism thus obtained, it has become possible to prepare cells or enzyme solution which has a significantly higher specific activity than a wild-type strain, which has been used as a DNA donor, and to extremely efficiently convert an L-amino acid amide, particularly an L-2-alkylcysteine amide into corresponding L-2-alkylcysteine.

The L-amino acid amide asymmetric hydrolase of the present invention has an activity to asymmetric hydrolyze not only an L-2-alkylcysteine but also an extremely wide substrate spectrum. Namely, the L-amino acid amide asymmetric hydrolase can asymmetrically hydrolyze various L-amino acid amides corresponding to natural typical amino acids such as L-alanine, L-valine, L-leucine, and L-phenylalanine, and L-amino acid amides corresponding to so-called atypical amino acids such as L-2-amino butyrate, L-t-leucine, L-phenylglycine, L-p-chlorophenyl glycine, L-allicin ethylene acetal, L-penicillamine, and (4R)-5,5-dimethyl-1,3-thiazolidin-4-carboxylic acid. As described above, the enzyme of the present invention is a novel enzyme having a strict stereospecificity that selectively hydrolyzes an amide bond in an L-amino acid amide and a property of reacting with a wide variety of L-amino acid amides, so it is an enzyme which is excellent in industrial applicability and different from known enzymes.

That is, the present invention relates to an L-amino acid amide asymmetric hydrolase described in the following (1), a DNA encoding the L-amino acid asymmetric hydrolase described in the following (2) or (3), a recombinant microorganism described in the following (4) or (5), a method of producing an L-amino acid from an L-amino acid amide by using the enzyme described in the following (6), and a method of producing an L-2-alkylcysteine from an L-2-alkylcysteine amide described in the following (7) to (9).

(1) An enzyme which stereoselectively hydrolyzes an amide bond of an L-amino acid amide, wherein said enzyme comprises an amino acid sequence represented by amino acid numbers 1 to 355 in SEQ ID NO: 8, or said amino acid sequence including deletion, substitution or addition of 1 or multiple amino acids.

(2) A DNA encoding an enzyme protein of the enzyme according to (1).

(3) The DNA according to (2), which comprises a nucleotide sequence represented by nucleotide numbers 868 to 1932 in SEQ ID NO: 7, or a nucleotide sequence which hybridizes with said nucleotide sequence under stringent conditions.

(4) A recombinant microorganism, into which the DNA according to (2) or (3) has been introduced.

(5) The recombinant microorganism according to (4), wherein the recombinant microorganism is *Escherichia coli*.

(6) A method of producing an L-amino acid, which comprises allowing an L-amino acid amide to react with the enzyme according to (1) to convert said L-amino acid amide into an L-amino acid.

(7) The production method according to (6), wherein the L-amino acid amide is a compound represented by the formula 1:

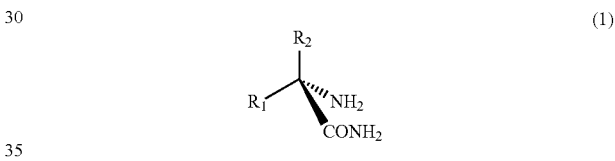

(1)

In the formula (1), $R_1$ represents hydrogen, a lower alkyl group, a substituted lower alkyl group, a phenyl group, a substituted phenyl group, a heterocyclic group, a substituted heterocyclic group, or a group which forms a nitrogen-containing heterocycle in combination with the carbon atom to which $R_1$ is bound and the amino group which is bound to the carbon atom. Here, examples of the lower alkyl group include an alkyl group having 1 to 4 carbon atoms. Examples of the substituted lower alkyl group include an alkyl group having 1 to 4 carbon atoms in which one or multiple hydrogen is substituted by a hydroxy group, a methoxy group, a mercapto group, a methylmercapto group, an amino group, a guanyl group, a carboxyl group, a carboxamide group, a halogen group, a phenyl group, a hydroxyphenyl group or an imidazolyl group. Examples of the substituted phenyl group include a phenyl group in which arbitrary hydrogen is substituted by a hydroxy group, a methoxy group, a mercapto group, a methylmercapto group, an amino group, a guanyl group, a carboxyl group, a carboxamide group or a halogen group. Examples of the heterocyclic group include an indolyl group and an imidazolyl group. Examples of the substituted heterocyclic group include a heterocyclic group such as the above-mentioned indolyl group or imidazolyl group, in which arbitrary hydrogen is substituted by a hydroxy group, a methoxy group, a mercapto group, a methylmercapto group, an amino group, a guanyl group, a carboxyl group, a carboxamide group, or a halogen group. Examples of the group which forms a nitrogen-containing heterocycle in combination with the carbon atom to which $R_1$ is bound and the amino group which is bound to the carbon atom include a pyrrolidine ring, a pyrrole ring, a thiazolidine ring, and an oxazolidine ring.

$R_2$ represents hydrogen or a lower alkyl group having 1 to 4 carbon atoms.

However, the compound in which $R_1$ and $R_2$ concomitantly represent hydrogen is excluded from the compound (1).

(8) The production method according to (6), in which the L-amino acid amide is a compound represented by the formula 2.

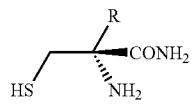

(2)

In the formula (2), R represents a lower alkyl group having 1 to 4 carbon atoms.

(9) The production method according to (8), in which R in the formula (2) is a methyl group.

The enzyme of the present invention may have an amino acid sequence represented by amino acid numbers 1 to 355 shown in SEQ ID NO: 8 in which 1 or multiple amino acids are deleted, substituted, or added, as long as the enzyme does not lose its activity. The number of the "multiple" amino acids is preferably 2 to 20, more preferably 2 to 10, and particularly preferably 2 to 5. The enzyme of the present invention may have not less than 80%, preferably not less than 90%, and more preferably not less than 95% homology to the amino acid sequence of SEQ ID NO: 8, and have an enzymatic activity to stereoselectively hydrolyze an amide bond in an L-amino acid amide.

In addition, a DNA encoding the enzyme of the present invention may be a DNA which hybridizes with a DNA having a nucleotide sequence of nucleotide numbers 868 to 1,932 of SEQ ID NO: 7 under stringent conditions, and encodes an enzyme which stereoselectively hydrolyzes an amide bond in an L-amino acid amide. Examples of the stringent condition include conditions under which DNAs having not less than 80%, preferably not less than 90%, more preferably not less than 95% homology hybridize with each other. Specific examples thereof include conditions under which hybridization reaction is performed and then washing is performed at 60° C., 1×SSC, 0.1% SDS, preferably at 60° C., 0.1×SSC, 0.1% SDS, and particularly preferably at 65° C., 0.1×SSC, 0.1% SDS.

DESCRIPTION OF THE PREFERRED EMBODIMENTS

Hereinafter, embodiments of the present invention will be described in detail.

A microorganism which serves as a donor of a DNA encoding the enzyme of the present invention is a microorganism which has an enzymatic activity to stereoselectively hydrolyze an amide bond in an L-amino acid amide, particularly an L-2-alkylcysteine amide. Examples of a method of finding such a microorganism include a method of selecting one from strains stocked in a type culture or the like, and a method of separating one from nature. The inventors of the present invention first examined stocked strains, and found that microorganisms belonging to the genus *Protaminobacter*, the genus *Mycoplana*, and the genus *Xnathobacter*, more specifically, *Protaminobacter alboflavus*, *Mycoplana ramose*, *Mycoplana dimorpha*, *Xanthobacter autotrophicus*, *Xanthobacter flavus* and the like corresponded to the microorganism having the above-mentioned enzymatic activity.

Next, separation of a more preferable strain from nature was intensively performed. As a result, the inventors succeeded in separating a novel strain identified as *Xanthobacter flavus* (*X. flavus*). The strain is a nonmotile gram-negative bacillus as shown by the following mycological properties (Table 1), and identified as a microorganism belonging to the genus *Xanthobacter* because it is polymorphic, catalase-positive, and oxidase-positive. Further, taxon of the microorganism was estimated by using a partial nucleotide sequence of about 500 by of 16SrDNA (16SrRNA gene), and as a result, the partial nucleotide sequence coincided with the nucleotide sequence of *X. flavus* with 100% homology and the strain locates at the same position as *X. flavus* on a molecular dendrogram, so the microorganism was identified as *X. flavus* and named NR303 strain.

TABLE 1

| Mycological property | |
|---|---|
| Cell morphology | Bacillus |
| Size | (0.5-0.6 × 2.0 μm) |
| Polymorphism | Present |
| Motility | Absent |
| Presence or absence of spore | Absent |
| Gram staining | – |
| Colony form (nutrient agar, 30° C., 24 hours) | |
| Round | |
| Entirely smooth | |
| Convex | |
| Glossy | |
| Cream color | |
| Growth temperature | |
| 37° C. | + |
| 40° C. | – |
| Catalase | + |
| Oxidase | + |
| Acid/gas production (glucose) | –/– |
| O/F test (glucose) | –/– |
| Reduction of nitrate | + |
| Production of indole | – |
| Acidification of glucose | – |
| Arginine dihydrolase | – |
| Urease | + |
| Escrine hydrolysis | – |
| Gelatin hydrolysis | – |
| β-galatosidase | – |
| Cytochrome oxidase | + |
| Assimilation property | |
| Glucose | – |
| L-arabinose | – |
| D-mannose | – |
| D-mannitol | – |
| N-acetyl-D-glucosamine | – |
| Maltose | – |
| Potassium gluconate | + |
| n-capric acid | – |
| Adipic acid | – |
| dl-malic acid | + |
| Sodium citrate | + |
| Phenyl acetate | – |
| Anaerobic growth | + |

A method of isolating a gene of the amino acid amid asymmetric hydrolase of *X. flavus* NR303 strain which has been newly separated by the inventors of the present invention, and a method of introducing the gene into *Escherichia coli* JM109 strain are described hereinafter as examples.

The culture of the DNA-donating microorganism is performed by using a medium containing a carbon source which can generally be assimilated, a nitrogen source, inorganic salts and nutrients necessary for each microorganism, and the like. During culture, pH in a range of 4 to 10 is preferable and temperature of 20 to 39° C. is preferable. The culture is aerobically performed for about 1 day to about 1 week.

Purification of the enzyme can be performed by using a general method for enzyme purification. That is, after completion of culture, cells are collected from the culture solution by a general procedure such as centrifugation or separation with a membrane, and then the cells are disrupted by a mechanical method such as ultrasonication. After that, residue is removed by centrifugation or the like to obtain crude enzyme solution. Next, the crude enzyme solution can be purified by subjecting it to salting out, adsorption chromatography, ion-exchange chromatography, hydrophobic chromatography, gel filtration chromatography, crystallization, or the like.

The N-terminal amino acid sequence of the purified enzyme is determined by using an automated Edman degradation amino acid sequencer, HPG 1005A protein sequencing system (Hewlett-Packard Development Company), and oligonucleotides (primers) for amplification by PCR are designed based on the determined N-terminal sequence. A chromosomal DNA extracted from *X. flavus* is used as a template and a DNA is amplified by PCR and labeled, to thereby obtain a probe.

A DNA extracted from *X. flavus* is partially digested with an appropriate restriction enzyme such as EcoRI. The DNA fragment and the labeled DNA probe are used to perform Southern hybridization. A DNA identified at this time is extracted and purified, and then ligated to an appropriate plasmid vector, to transform *Escherichia coli* (*E. coli*).

The labeled DNA probe is used for colony hybridization to obtain a cloned plasmid containing the DNA fragment of interest. By using the plasmid, the nucleotide sequence of the DNA derived from *X. flavus* which has been incorporated into the vector is determined. The open reading flame of the amino acid sequence of the L-amino acid amide asymmetric hydrolase gene is identified in the determined nucleotide sequence, to thereby confirm the presence of entire coding region of the L-amino acid amide asymmetric hydrolase gene in the DNA fragment obtained in the above-mentioned step.

Primers are designed on the basis of the nucleotide sequence of the resultant L-amino acid amide asymmetric hydrolase gene. A chromosomal DNA extracted from *X. flavus* is used as a template to amplify the above-mentioned DNA by PCR, and the obtained DNA is ligated to a plasmid vector pUC19. The resultant plasmid is named pMCA1. The pMCA1 is used to transform *E. coli* JM109, and the recombinant bacterium having the L-amino acid amide asymmetric hydrolase gene is named pMCA1/JM109.

The obtained transformant pMCA1/JM109 has been deposited in International Patent Organism Depositary, National Institute of Advanced Industrial Science and Technology (Tsukuba Central 6, 1-1-1 Higashi, Tsukuba, Ibaraki, Japan, Postal code 305-5466) as the accession number FERM AP-20056 on May 21, 2004, and then transferred to international deposit under Budapest Treaty and given an accession number of FERM BP-10334. Thus, a DNA encoding the enzyme of the present invention can also be obtained from the plasmid pMCA1 held by the transformant. For instance, the plasmid pMCA1 may be digested with a restriction enzyme which recognizes the sequence present in the multicloning site of pUC19 to obtain the above-mentioned DNA, or the plasmid pMCA1 may be used as a template to perform PCR using primers designed on the basis of the nucleotide sequence of SEQ ID NO: 7, to thereby obtain the above-mentioned DNA.

Meanwhile, the DNA of the present invention can be obtained from a chromosome of other strain of *X. flavus* or a microorganism other than *X. flavus*. For instance, by using a probe designed on the basis of the nucleotide sequence of SEQ ID NO: 7, a DNA encoding the above-mentioned enzyme derived from any one of the above-mentioned microorganisms can be isolated from a chromosomal DNA of the microorganism by hybridization reaction.

A vector for introducing the DNA of the present invention into a host microorganism may be any plasmid vector such as pUC 18, pUC 19, and pUC 118 and phage vectors such as λgt11. Further, the DNA of the present invention can be directly incorporated into the chromosome of a host microorganism without using a vector. Examples of a host microorganism to be used for transformation include, but not limited to, bacteria belonging to the genus *Escherichia* such as JM105 strain and JM109 strain of *E. coli*.

Operations required for handling a DNA or *E. coli* as a recombination host are those generally performed by one skilled in the art, and the operations can be easily performed according to, for example, Molecular Cloning: A Laboratory Manual, 3rd Ed. (ed. Sambrook J. and Russel D. W.), Cold Spring Harbor Laboratory Press, Cold Spring Harbor, N.Y., 2001 (hereinafter, described as Molecular Cloning 3rd Ed.). Enzymes, reagents and the like to be used are all commercially available products, and the purposes of them can be fully attained according to the designated usage condition unless otherwise noted. Extraction of a whole DNA from bacteria can be performed according to, for example, the method of Saito et al. (Biochim. Biophys. Acta., 72, 619-629, 1963). In addition, labeling of a DNA can be performed by using radioactive isotope or nonradioactive compounds such as digoxigenin, biotin and fluorescein, which are conventionally and generally used, and can be easily performed by using Rediprime™ II Random Prime Labelling System (Amersham Pharmacia Biotech), AlkPhos™ Direct Labelling and Detection System (Amersham Pharmacia Biotech), or the like. Determination of a nucleotide sequence of DNA can also be performed by using a known method described in Molecular Cloning 3rd Ed. or the like. For instance, the determination can be easily performed by using an apparatus such as Li-Cor DNA Sequencer model 4000L according to an attached manual instruction. In addition, hybridization can be performed according to the method described in Molecular Cloning 3rd Ed. or the like.

Culture of the transformant microorganism of the present invention is performed by using a medium containing a carbon source which can be generally assimilated, a nitrogen source, inorganic salts and nutrients necessary for the microorganism and the like. During culture, pH in a range of 4 to 10 is preferable and temperature of 20 to 50° C. is preferable. Culture is aerobically performed for about 1 day to about 1 week. From the transformant microorganism thus cultured, the enzyme of the present invention can be obtained by a general purification method. The thus-obtained enzyme can be used for a reaction of stereoselectively producing L-amino acid from L-amino acid amide such as the compound represented by the formula (I). In a case where a mixture of D- and L-amino acid amides such as a racemic compound is a substrate, a mixture of L-amino acid and D-amino acid amide is obtained. In this case, the L-amino acid and the D-amino acid amide are obtained respectively by separating them from each other, and the separated D-amino acid amide is independently subjected to hydrolysis to thereby obtain D-amino acid. In addition, in a case where a substrate of an enzymatic reaction is only composed of an L-amino acid amide, an L-amino acid corresponding to the L-amino acid amide is obtained. Cells or cell processed product of the transformant may also be used for the above-mentioned reaction. For instance, culture solution containing cells, separated cells, disrupted cells or the like can be used for the above-mentioned reaction. Further, cells or enzyme may be immobilized according to the general method and used.

Reaction conditions vary depending on a kind and amount of L-amino acid amide contained in reaction solution. However, concentration of an amino acid amide as a raw material in reaction solution is 0.1 to 40 wt %, and an amount of the enzyme is 0.00001 to 3 folds or, in general, preferably 0.00005 to 0.001 folds of the weight of the raw material amino acid amide on the basis of dry cells of the recombinant microorganism containing the enzyme. Reaction temperature is 10 to 70° C. and preferably 20 to 60° C., and pH is 4 to 13, preferably 5 to 10, or more preferably 6 to 9. Meanwhile, 2-alkylcysteine amide and 2-alkylcysteine are apt to be oxidized and become a dimerized disulfide when they are left under the presence of oxygen. In order to prevent this phenomenon, a biochemical asymmetric hydrolysis reaction is preferably performed under an inert gas atmosphere such as nitrogen, but a method which comprises allowing a reductive material such as 2-mercaptoethanol to coexist in the system can also be employed. Meanwhile, when all solvents to be used in the reaction are deaerated before the reaction is performed, no by-product is produced, so the reaction advantageously proceeds. When the reaction is performed, addition of such a metal ion as Mg, Cu, Zn, Fe, Mn, Ni, Co to the reaction system can further increase reaction velocity. The amount to be added cannot be generally stated because it varies depending on the kind of the metal ion, but such a metal ion is desirably added at a concentration of preferably 1 to 50 ppm, or more preferably 5 to 20 ppm. For instance, when 5 to 20 ppm of a divalent Mn ion is added, the reaction velocity significantly increases to 2 to 5 folds as compared to the case where no ion is added. On the other hand, cells or cell processed products which have been used in the asymmetric hydrolysis reaction can be collected by means of centrifugation, filtration procedure or the like, to be reused as an enzymatic catalyst for the asymmetric hydrolysis reaction. When the concentration of the raw material amino acid amide in the reaction solution is high, the amount of the enzyme with respect to the amino acid amide is appropriately selected such that the ratio of the amount to be used is 3 folds, which is the upper limit of the preferable range, or less than 3 folds, under which ratio the reaction can be preferably performed.

Separation of an L-amino acid produced in the asymmetric hydrolysis reaction of DL-amino acid amides from an unreacted D-amino acid amide can be performed by utilizing, but not particularly limited to, a method which comprises removing microbial cells from the solution obtained after completion of the reaction by general solid-liquid separation means such as centrifugation or a filtration membrane, and then concentrating the resultant solution under reduced pressure and adding an organic solvent to thereby precipitate the amino acid; or a known method such as recrystallization or column chromatography. An ion-exchange electrodialysis method or a separation method utilizing adsorption/desorption with an ion-exchange resin is also effective.

The L-amino acid amide asymmetric hydrolase of the present invention has a characteristic of efficiently hydrolyzing an amide bond in an L-2-alkylcysteine amide, and in addition, has an extremely wide substrate spectrum, so L-amino acids corresponding to various L-amino acid amides can be produced by using the enzyme of the present invention. Specific examples of the amino acids include, in addition to 2-methyl-L-cysteine, protein-consisting amino acids such as L-alanine, L-valine, L-leucine and L-phenylalanine, and further include so-called non-protein amino acids such as L-2-amino butyrate, L-t-leucine, L-phenylglycine, L-p-chlorophenyl glycine, L-allicine ethylene acetal, L-penicillamine, and (4R)-5,5-dimethyl-1,3-thiazolidin-4-carboxylic acid.

EXAMPLES

The present invention will be described in more detail by referring to examples and comparative examples, but the present invention is not limited thereto.

Example 1

Isolation of Amino Acid Amide Asymmetric Hydrolase

*Xanthobacter flavus* NR303 strain was inoculated into 3 L of a medium having the composition shown in the following Table 2 and cultured at 30° C. for 170 hours, and then cells were obtained by centrifugation. 240 g in wet weight of the cells were disrupted by means of ultrasonic and the resultant was subjected to centrifugation, to thereby prepare a cell-free extract.

TABLE 2

| Medium composition | |
|---|---|
| $(NH_4)_2SO_4$ | 3 g |
| $KH_2PO_4$ | 1.4 g |
| $Na_2HPO_4$ | 3 g |
| $NaHCO_3$ | 0.3 g |
| $MgSO_4 \cdot 7H_2O$ | 0.2 g |
| 2% $CaCl_2$ | 1 g |
| Yeast extract | 0.2 g |
| Vitamin mixture | 1 g |
| Urea | 1 g |
| Glycerin | 10 g |
| Trace mineral | 3.5 g |

1 L (pH 7.0)

Ammonium sulfate was added to the cell-free extract to be 30% saturation, and centrifugation was performed to remove precipitates. After that, ammonium sulfate was further added to the supernatant to be 60% saturation. The generated precipitates were collected by centrifugation and dissolved in 100 mM potassium phosphate buffer, and the resultant solution was subjected to dialysis against 10 mM potassium phosphate buffer. The resultant was adsorbed to a DEAE-Toyopearl resin (Tosoh Corporation) which had been equilibrated with 10 mM potassium phosphate buffer, followed by ion-exchange chromatography. The obtained fraction exhibiting an amino acid amide asymmetric hydrolase activity was subjected to column chromatography by sequentially using Butyl-Toyopearl column (Tosoh Corporation) and Gigapite column (Seikagaku Corporation), each using ammonium sulfate. The resultant purified enzyme was separated by SDS-PAGE, to thereby confirm that the purified enzyme showed a single band and had a molecular weight of 40,000.

Example 2

Analysis of N-Terminal Amino Acid Sequence

The N-terminal amino acid sequence of the polypeptide purified in Example 1 was analyzed by using an automated Edman degradation amino acid sequencer, HP G1005A Protein Sequencing System (Hewlett-Packard Development Company). The amino acid sequence is represented by SEQ ID NO: 1.

Example 3

Acquisition of a DNA Fragment of the Present Invention

*X. flavus* was inoculated into 5.0 mL of a medium having the composition shown in Table 1 and cultured at 30° C. for 48 hours. Microbial cells were obtained by centrifugation, and a chromosomal DNA of the microorganism was obtained by a phenol-chloroform method. Primers each having a sequence of SEQ ID NO: 2 (AF), SEQ ID NO: 3 (BF), SEQ ID NO: 4 (AR), or SEQ ID NO: 5 (BR) were designed from the amino acid sequence determined in Example 2. PCR was performed in the presence of a heat-resistant DNA polymerase with addition of any 2 kinds of the 4 primers. The products of PCR were subjected to agarose gel electrophoresis. As a result, a 87 by DNA was specifically amplified in a reaction solution in which the primer BF (SEQ ID NO: 3) and the primer AR (SEQ ID NO: 4) were used, so the DNA was extracted and purified from agarose electrophoresis gel. A portion of the DNA was cloned into pT7Blue T-Vector (Novagen) and the nucleotide sequence (SEQ ID NO:6) thereof was determined by using Li-Cor DNA Sequencer model 4000L according to an operation method according to the attached manual instruction. The remaining of the purified 87 by DNA which had been amplified by the Degener PCR was labeled by using Rediprime™ II Random Prime Labelling System (Amersham Pharmacia Biotech).

Example 4

Southern Hybridization of *X. flavus* Chromosomal DNA Library

A chromosomal DNA of *X. flavus* was obtained by the method described in Example 3. The DNA was digested with EcoRI, and then Southern hybridization was performed by using the labeled 87 by DNA prepared in Example 3 as a probe. The procedure was according to Molecular Cloning 3rd Ed. As a result, a DNA band of about 5 kb was detected. The DNA was extracted and purified from the agarose gel and inserted into an EcoRI site of pBluescript II SK(-) (Strategene), and the resultant was introduced into *E. coli* JM109 by a transforming method using calcium chloride.

Example 5

Colony Hybridization and Subcloning

The transformant strain of *E. coli* JM109 obtained in Example 4 was applied onto an LB agar medium (1-L aqueous solution containing 10.0 g of Bacto Trypton, 5.0 g of Bacto Yeast Extract, 10.0 g of sodium chloride, and 15.0 g of agar) containing 50 µg/mL ampicillin, and cultured overnight at 37° C. The appeared colonies were lifted with a nitrocellulose membrane, CELLULOSE NITRATE (Advantec Toyo Kaisha, Ltd.), and hybridization was performed by using the DNA probe obtained in Example 3. As a result of the hybridization, a plasmid was obtained from a positive clone and the nucleotide sequence thereof (SEQ ID NO: 7) was determined by using Li-Cor DNA Sequencer model 4000L.

Example 6

Construction of an Expression Plasmid and Transformation of *E. coli*

PCR was performed by using a chromosomal DNA extracted from *X. flavus* as a template and primers MCA-F and MCA-R (SEQ ID NOS: 9 and 10). The resultant PCR product was purified and digested with restriction enzymes HindIII and XbaI. The resultant was ligated to pUC 19 (TAKARA BIO INC.) which had been digested with the same enzymes to prepare pMCA1, which was used to transform *E. coli* JM109 by the calcium chloride method. The transformant strain was applied on an LB agar medium containing 50 µg/mL ampicillin and a clone which grew thereon was obtained as a transformant strain pMCA1/JM109.

Example 7

Asymmetric Hydrolysis of 2-Methylcysteine Amide Racemic Mixture by Using the Transformant: Addition of Manganese Chloride A medium having a composition as shown in the following Table 3 was prepared, and 200 mL of the medium was poured into 1-L conical flask and sterilized. After that, the medium was added with 50 µg/mL ampicillin and then inoculated with the transformant strain pMCA1/JM109, followed by shaking culture at 37° C. for 15 hours. Subsequently, the culture solution was subjected to centrifugation, to thereby obtain living cells corresponding to 0.1 g of dry cells.

TABLE 3

| Medium composition | |
|---|---|
| pH | 7.0 |
| Triptone | 1% |
| Yeast extract | 0.5% |
| Sodium chloride | 0.5% |

10.0 g (58.6 mmol) of a racemic mixture of 2-methylcysteine amide hydrochloride was dissolved into 300 mL of 50 mM phosphate buffer (pH 7.0). After that, the mixture was poured into 500-mL flask, which was added with an aqueous manganese chloride solution such that the concentration of a divalent Mn ion became 10 ppm, and further added with the living cells corresponding to 0.01 g of dry cells, followed by stirring culture at 30° C. for 24 hours under a nitrogen stream to allow a hydrolysis reaction to proceed.

After completion of the reaction, the reaction solution was subjected to centrifugation to remove the cells therefrom, and a supernatant was obtained. The supernatant was added with 1 g of activated carbon and stirred for 1 hour. After that, the activated carbon was separated by filtration and then water was distilled off with an evaporator under reduced pressure. The resultant was added with 20 mL of 2-propanol, and the whole was stirred under heating and then cooled to 5° C., followed by filtration to collect precipitated crystals. The crystals collected by filtration were recrystallized by addition of ethanol, to thereby obtain 3.04 g (22.5 mmol) of 2-methyl-L-cysteine. The isolation yield from 2-methyl-L-cysteine amide in the racemic mixture which had been introduced into the reaction was 76.8 mol %, and the isolation yield from the racemic mixture of 2-methylcysteine amide was 38.4%. In addition, the solid was analyzed under the HPLC condition A as shown in the following Table 4, and as a result, the optical purity of the solid was not less than 98% e.e.

TABLE 4

HPLC condition A

Column: Sumichiral OA-5000 (Sumika Chemical Analysis Service, Ltd.)
Column temperature: 60° C.
Eluting solution: 3 mM aqueous $CuSO_4$ solution
Flow rate: 1.0 mL/min
Detection: CD-2095plus (JASCO Corporation)
Sample: 50 µL of 0.1% solution after a formalin treatment was injected.

Example 8

Asymmetric Hydrolysis of 2-Methylcysteine Amide Racemic Mixture by Using the Transformant: No Addition of Manganese Chloride A biochemical asymmetric hydrolysis reaction was performed in the same manner as in Example 7 except that the aqueous manganese chloride solution was not added. The reaction was performed at 30° C. for 24 hours and the same after-treatment as in Example 7 was performed, to thereby obtain 1.50 g (11.1 mmol) of 2-methyl-L-cysteine. The isolation yield from 2-methyl-L-cysteine amide was 37.9 mol %, the isolation yield from 2-methylcysteine amide was 18.9 mol %, and the optical purity was not less than 98% e.e.

Comparative Example 1

Asymmetric Hydrolysis of 2-Methylcysteine Amide Racemic Mixture by Using a Wild-Type Microorganism (0.01 g of Cells)

A medium having a composition as shown in the following Table 5 was prepared, and 200 mL of the medium was poured into a 1-L conical flask and sterilized. After that, *X. flavus* was inoculated thereto and shaking culture was performed at 30° C. for 170 hours. Subsequently, the culture solution was subjected to centrifugation, to thereby obtain living cells corresponding to 0.1 g of dry cells.

TABLE 5

| Medium composition | |
|---|---|
| $(NH_4)_2SO_4$ | 3 g |
| $KH_2PO_4$ | 1.4 g |
| $Na_2HPO_4$ | 3 g |
| $NaHCO_3$ | 0.3 g |
| $MgSO_4 \cdot 7H_2O$ | 0.2 g |
| 2% $CaCl_2$ | 1 g |
| Yeast extract | 0.2 g |
| Vitamin mixture | 1 g |
| Urea | 1 g |
| Glycerin | 10 g |
| Trace mineral | 3.5 g |

1 L (pH 7.0)

10.0 g (58.6 mmol) of racemic mixture of 2-methylcysteine amide hydrochloride was dissolved into 300 mL of 50 mM phosphate buffer (pH 7.0). After that, the mixture was poured into a 500-mL flask, which was added with an aqueous manganese chloride solution such that the concentration of a divalent Mn ion became 10 ppm, and further added with the living cells corresponding to 0.01 g of dry cells, followed by stirring culture at 30° C. for 24 hours under a nitrogen stream to allow a hydrolysis reaction to proceed. After completion of the reaction, the reaction solution was subjected to centrifugation to remove the cells, and the supernatant was analyzed under the HPLC condition B as shown in the following Table 6. As a result, no 2-methylcysteine as a product was observed.

TABLE 6

HPLC condition B

Column: LiChrosorb 100 RP-18 (KANTO CHEMICAL CO., INC.)
Column temperature: 40° C.
Eluting solution: 50 mM aqueous $HClO_4$ solution
Flow rate: 0.5 mL/min
Detection: RI
Sample: 5 µL of 0.1% aqueous solution was injected.

Comparative Example 2

Asymmetric Hydrolysis of 2-Methylcysteine Amide Racemic Mixture by Using a Wild-Type Microorganism (5 g of Cells)

10 L of the culture solution obtained after culture in the medium composition in Comparative Example 1 was subjected to centrifugation, to thereby obtain living cells corresponding to 5 g of dry cells of *X. flavus*. 10.0 g (58.6 mmol) of a racemic mixture of 2-methylcysteine amide hydrochloride was dissolved into 300 mL of 50 mM phosphate buffer (pH 7.0). After that, the mixture was poured into 500-mL flask, which was added with an aqueous manganese chloride solution such that the concentration of a divalent Mn ion became 10 ppm, and further added with the living cells corresponding to 5 g of dry cells, followed by stirring culture at 30° C. for 24 hours under a nitrogen stream to allow a hydrolysis reaction to proceed. After completion of the reaction, the reaction solution was subjected to centrifugation to remove the cells therefrom, and the supernatant was analyzed under the HPLC condition B. As a result, it was confirmed that 28.2 mmol of 2-methylcysteine was produced. In addition, the supernatant was analyzed under the HPLC condition A, and as a result, the optical purity of the L-amino acid was not less than 98% e.e.

Comparative Example 3

Asymmetric Hydrolysis of 2-Methylcysteine Amide Racemic Mixture by Using a Wild-Type Microorganism: No Addition of Manganese Chloride A biochemical asymmetric hydrolysis reaction was performed in the same manner as in Comparative Example 2 except that the aqueous manganese chloride solution was not added. The reaction was performed at 30° C. for 24 hours. After completion of the reaction, the reaction solution was subjected to centrifugation to remove the cells therefrom, and then the supernatant was analyzed under the HPLC condition B. As a result, it was confirmed that 13.9 mmol of 2-methylcysteine was produced. In addition, the supernatant was analyzed under the HPLC condition A, and as a result, the optical purity of the L-amino acid was not less than 98% e.e.

Example 9

Asymmetric Hydrolysis of Racemic Compounds of Various Amino Acid Amides by Using the Transformant Enzymatic reactions were performed by using a culture solution of the transformant strain pMCA 1/JM109 which had been cultured in the same manner as in Example 7 and a racemic mixture of various amino acid amides as a substrate. Each of the substrate compound was dissolved into 50 mM phosphate buffer (pH 7.0) such that the substrate concentration was adjusted to 0.1%, and the substrate solution was added with the cells to perform an enzymatic reaction at 30° C. After completion of the reaction, the reaction solution was subjected to centrifugation to remove the cells therefrom, and the stereoselectivity and reaction rate (reaction rate=mol amount of amino acid after completion of the reaction/(mol amount of amino acid amide after the reaction+mol amount of amino acid after the reaction)×100) were analyzed under the HPLC condition A and the HPLC condition B. Table 7 shows the results. In any of the reactions, selectivity of hydrolysis is selective to an L-form, and optical purity of the produced L-amino acid was not less than 98% e.e.

TABLE 7

Results of reactions of various amino acid amides

| Substrate | Substrate weight/ dry cell weight | Reaction time | Reaction rate |
| --- | --- | --- | --- |
| Valine amide | 0.01 | 24 hr | 44.3% |
| 2-amino butyrate amide | 0.1 | 5 hr | 49.2% |
| t-leucine amide | 0.1 | 24 hr | 44.4% |

TABLE 7-continued

Results of reactions of various amino acid amides

| Substrate | Substrate weight/ dry cell weight | Reaction time | Reaction rate |
| --- | --- | --- | --- |
| Allicin amide ethylene acetal | 0.01 | 24 hr | 44.3% |
| Phenylglycine amide | 0.01 | 5 hr | 48.8% |
| p-chlorophenyl glycine amide | 0.01 | 5 hr | 49.6% |
| Phenylalanine amide | 0.01 | 5 hr | 47.8% |
| penicillamine amide | 0.01 | 5 hr | 44.9% |
| 5,5-dimethylthiazolidin-4-carboxylate amide | 0.1 | 24 hr | 47.0% |

INDUSTRIAL APPLICABILITY

The present invention provides a preferable method of producing an optically active amino acid, particularly an optically active 2-alkylcysteine, which is a compound extremely useful from the industrial viewpoint and is expected to be widely utilized as a production intermediate of various industrial chemicals, pharmaceuticals, and agricultural chemicals.

What is claimed is:

1. An isolated DNA which encodes an enzyme which comprises an amino acid sequence not less than 95% homologous to the amino acid sequence of SEQ ID NO: 8, and has an enzymatic activity to stereoselectively hydrolyze an amide bond in an L-amino acid amide.

2. The DNA according to claim 1, which comprises the nucleotide sequence represented by nucleotide numbers 868 to 1932 in SEQ ID NO: 7, or a nucleotide sequence which hybridizes with said nucleotide sequence under stringent conditions, wherein said stringent conditions comprise washing at 65° C., 0.1×SSC, 0.1% SDS.

3. A recombinant microorganism, into which the DNA according to claim 1 has been introduced.

4. A recombinant microorganism, into which the DNA according to claim 2 has been introduced.

5. The recombinant microorganism according to claim 3, wherein the recombinant microorganism is *Escherichia coli*.

6. The recombinant microorganism according to claim 4, wherein the recombinant microorganism is *Escherichia coli*.

7. A method of producing an L-amino acid, which comprises allowing an L-amino acid amide to react with the recombinant microorganism according to claim 3 to convert said L-amino acid amide into an L-amino acid.

8. The production method according to claim 7, wherein the L-amino acid amide is a compound represented by formula 1:

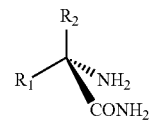
(1)

wherein $R_1$ represents hydrogen, a lower alkyl group, a substituted lower alkyl group, a phenyl group, a substituted phenyl group, a heterocyclic group, a substituted heterocyclic group, or a group which forms a nitrogen-containing heterocycle in combination with the carbon atom to which $R_1$ is bound and the amino group which is bound to the carbon atom, and $R_2$ represents hydrogen or a lower alkyl group having 1 to 4 carbon atoms, with the proviso that a case where $R_1$ and $R_2$ concomitantly represent hydrogen is excluded.

9. The production method according to claim 7, wherein the L-amino acid amide is a compound represented by formula 2:

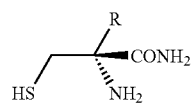
(2)

wherein R represents a lower alkyl group having 1 to 4 carbon atoms.

10. The production method according to claim 9, wherein R in formula 2 is a methyl group.

11. A method of producing an L-amino acid, which comprises allowing an L-amino acid amide to react with the recombinant microorganism according to claim 4 to convert said L-amino acid amide into an L-amino acid.

12. The production method according to claim 11, wherein the L-amino acid amide is a compound represented by formula 1:

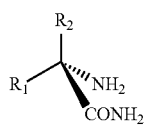

(1)

wherein $R_1$ represents hydrogen, a lower alkyl group, a substituted lower alkyl group, a phenyl group, a substituted phenyl group, a heterocyclic group, a substituted heterocyclic group, or a group which forms a nitrogen-containing heterocycle in combination with the carbon atom to which $R_1$ is bound and the amino group which is bound to the carbon atom, and $R_2$ represents hydrogen or a lower alkyl group having 1 to 4 carbon atoms, with the proviso that a case where $R_1$ and $R_2$ concomitantly represent hydrogen is excluded.

13. The production method according to claim 11, wherein the L-amino acid amide is a compound represented by formula 2:

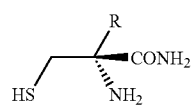

(2)

wherein R represents a lower alkyl group having 1 to 4 carbon atoms.

14. The production method according to claim 13, wherein R in formula 2 is a methyl group.

* * * * *

UNITED STATES PATENT AND TRADEMARK OFFICE
CERTIFICATE OF CORRECTION

PATENT NO. : 7,776,570 B2
APPLICATION NO. : 12/174995
DATED : August 17, 2010
INVENTOR(S) : Asano et al.

It is certified that error appears in the above-identified patent and that said Letters Patent is hereby corrected as shown below:

Title Page 1, Column 2, Line 18, *"Rhodopseudomans palustris"* should be changed to --*Rhodopseudomonas palustris*--

Column 3, Line 7, "1994" should be changed to --1994.--

Column 5, Line 63, "the genus *Xnathobacter*," should be changed to --the genus *Xanthobacter*,--

Column 6, Line 10, "about 500 by" should be changed to --about 500 bp--

Column 6, Line 43, "β-galatosidase" should be changed to --β-galactosidase--

Column 10, Line 52, "and Gigapite" should be changed to --and Gigabyte--

Column 11, Line 19, "by DNA was" should be changed to --bp DNA was--

Column 11, Line 28, "87 by DNA" should be changed to --87 bp DNA--

Column 11, Line 42, "87 by DNA" should be changed to --87 bp DNA--

Column 11, Lines 47-48, "(Strategene), and" should be changed to --(Stratagene), and--

Column 11, Line 57, "of Bacto Trypton," should be changed to --of Bacto Tryptone,--

Signed and Sealed this
Twenty-ninth Day of March, 2011

David J. Kappos
*Director of the United States Patent and Trademark Office*

SEQUENCE LISTING

```
<160> NUMBER OF SEQ ID NOS: 10

<210> SEQ ID NO 1
<211> LENGTH: 40
<212> TYPE: PRT
<213> ORGANISM: Xanthobacter flavus

<400> SEQUENCE: 1

Ala Ser Arg Pro Leu Thr Pro Pro Pro Tyr Ser Pro Pro Asp Pro Ala Trp
  1               5                  10                  15

Leu Glu Gly Ser Ile Met Ala Ala Arg Gly Glu Ala Lys Gly Arg Ala Gly
             20                  25                  30

Glu Arg Tyr Glu Ile Thr
 35                  40

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 2
cgsccsctsa csccsccscc                                                   20

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 3
ccsccsgayc csgcstggctsg                                                 22

<210> SEQ ID NO 4
```

-continued

```
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 4
sgtgatytcr tascgytcgcc                                                  21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 5
sgcscggccc ttsgcytcgcc                                                  21

<210> SEQ ID NO 6
<211> LENGTH: 87
<212> TYPE: DNA
<213> ORGANISM: Xanthobacter flavus
<220> FEATURE:

<400> SEQUENCE: 6
cctcccgatc cggcctggct cgaaggctcc atcatggctg cccgcggcga agccaaaggg       60
cgcgccggcg aacgctacga gatcacc                                           87

<210> SEQ ID NO 7
<211> LENGTH: 4840
<212> TYPE: DNA
<213> ORGANISM: Xanthobacter flavus
<220> FEATURE:
<221> NAME/KEY: CDS
<222> LOCATION: (868)..(1932)

<400> SEQUENCE: 7
gaattcgata ttatccgcga ggagccggcg cccatccggc cggatcccta tctggtgcgc       60
tccgcgccca ccgacagctg gttcgcatcc gcgccgcgct gcggtcgcca agtaaggagc      120
gggcgagcca tgtcccgcaa cctgctccag aacttccgcg gcgcccgggc gctcatcgtc      180
gcctccggcg agggcggcat cgacacgctg gagagcgtgc tcggcaagct cggcctcttg      240
gtcgcccgct cggaggcgcc ggaggcgggc cgccatctcg acctcgcctc ggtggaggag      300
cgcgcggacc tgctcttcat cgacggcgac ctcgacagcg tgctgccctg cgacctcggc      360
gcggcccgca ccccgccggt gccggtgatc gggctggtcg catcgaggc gccgggccgg       420 ctgaaggcgt tgatgaacca gggggccacg gccttcctgc gcaagccggt ctatgccggc      480
gccgtctaca ccacgctgtt cctcggcgtg aaccagtatc tgctgcgcaa ggagatggcg      540
agcgagctga cgcccagca ggatcgccgc cgccgccgca aggcggtcat caagaccatc      600
ctgctgctga tggaagagca ccaggtggat gacgacgagg cctatgtcat gctccgccgc      660
gacagcatgc gccggcgcca gagcctcgag gattattgcg aggactacat ctccggccgg      720
tcgaagctga ccgcgtcctc gccgaagcc gagccgcgca ccgcggcccg gcgctgacct       780
taccgaccca catcacgacg gagccgcccg gctccgccgc acgtggcagc tgccagcgac      840
gccagcccgc ccgcaaggag aaggccc atg tcc cgg cat ccc atg tcc cgg cag      894
                                Met Ser Arg His Pro Met Ser Arg Gln
                                 1               5
```

```
cac gca tca cgg cct ctg acg ccg ccc ccc tat tcc cct ccc gat ccg gcc   945
His Ala Ser Arg Pro Leu Thr Pro Pro Pro Tyr Ser Pro Pro Asp Pro Ala
 10              15                  20                  25 tgg ctc gaa ggc tcc atc atg gct gcc cgc ggc gaa gcc aaa ggg cgc gcc   996
Trp Leu Glu Gly Ser Ile Met Ala Ala Arg Gly Glu Ala Lys Gly Arg Ala
                 30                  35                  40 ggc gaa cgc tac gag atc acc gag gcg agc caa ggc aag tat cac tac gtc  1047
Gly Glu Arg Tyr Glu Ile Thr Glu Ala Ser Gln Gly Lys Tyr His Tyr Val
         45                  50                  55                  60 tac ggc ccg tat gcc acg ccc gtg ctg cgc gtg gat ccg ggc gcg gtg gtg  1098
Tyr Gly Pro Tyr Ala Thr Pro Val Leu Arg Val Asp Pro Gly Ala Val Val
 61              65                  70                  75 agc gcc gag acc cac gac gcc atg gaa ggg cag atc aaa agc gag agc gac  1149
Ser Ala Glu Thr His Asp Ala Met Glu Gly Gln Ile Lys Ser Glu Ser Asp
                 80                  85                  90 aag ccg tcg gaa atc ctc aac ttt ccc ttc ctc aac ccg cag aat ggg ccg  1200
Lys Pro Ser Glu Ile Leu Asn Phe Pro Phe Leu Asn Pro Gln Asn Gly Pro
 95             100                 105                 110 atc ttc gtc aac ggc gcg gag aag ggc gac tgc ctc gcc gtc tat atc cac  1251
Ile Phe Val Asn Gly Ala Glu Lys Gly Asp Cys Leu Ala Val Tyr Ile His
                115                 120                 125 gac atc gtg ccg cgc ggg ccg cag ccc atc ggc acc acc tgc atc atg ccg  1302
Asp Ile Val Pro Arg Gly Pro Gln Pro Ile Gly Thr Thr Cys Ile Met Pro
130                 135                 140                 145 gag ttc ggc ggc ctc gtc ggc aca ggc gac acc gcg atc ctc aac gcg cct  1353
Glu Phe Gly Gly Leu Val Gly Thr Gly Asp Thr Ala Ile Leu Asn Ala Pro
                150                 155                 160 ttg ccg gag atc gtg aag aag ctg cac gtg gat ccg gcg act ggc gtg cgc  1404
Leu Pro Glu Ile Val Lys Lys Leu His Val Asp Pro Ala Thr Gly Val Arg
        165                 170                 175 tgg aac gag cga atc agc ctg ccc tac cag ccc ttc atc ggc acc atc ggc  1455
Trp Asn Glu Arg Ile Ser Leu Pro Tyr Gln Pro Phe Ile Gly Thr Ile Gly
180                 185                 190                 195 acc gcg ccg gag atc gag gcc att tcc tcc ctc gtc ccc gac tat tac ggc  1506
Thr Ala Pro Glu Ile Glu Ala Ile Ser Ser Leu Val Pro Asp Tyr Tyr Gly
                200                 205                 210 ggc aac atg gac ctg ccg gac gtg gct ccc ggc gcc gtc atc tac ctg ccg  1557
Gly Asn Met Asp Leu Pro Asp Val Ala Pro Gly Ala Val Ile Tyr Leu Pro
        215                 220                 225                 230 gtc cat gcg ccc ggc gcc ctg ctc tat ctc ggc gat tgc cac gcc gcg cag  1608
Val His Ala Pro Gly Ala Leu Leu Tyr Leu Gly Asp Cys His Ala Ala Gln
                    235                 240                 245 ggc gat ggg gag ctg tgt gga ttc gcc atc gag cat ccc acc gtg acc acg  1659
Gly Asp Gly Glu Leu Cys Gly Phe Ala Ile Glu His Pro Thr Val Thr Thr
        250                 255                 260 gtg cag atc gac ctc atc aag ggg tgg aac ttc cgc tgg ccg cgg ctg gag  1710
Val Gln Ile Asp Leu Ile Lys Gly Trp Asn Phe Arg Trp Pro Arg Leu Glu
265                 270                 275                 280 acc cac gac cgc atc atg acc atc ggc tcc ggc cgc ccc atg gag gac gcc  1761
Thr His Asp Arg Ile Met Thr Ile Gly Ser Gly Arg Pro Met Glu Asp Ala
                285                 290                 295 gcc cgc atc gcc tat cga gaa ctg gtg cgc tgg atg gcc gac tac ggg       1812
Ala Arg Ile Ala Tyr Arg Glu Leu Val Arg Trp Met Ala Asp Tyr Gly
        300                 305                 310                 315 tat gac gag ctg gaa gcc tac atg ctg ctg acg cag gcc ggg cac ctc agg  1863
Tyr Asp Glu Leu Glu Ala Tyr Met Leu Leu Thr Gln Ala Gly His Leu Arg
                320                 325                 330 gtc ggc aac atg gtg gac ccg aag tac acg ctc ggc gcc tcc gtc gac aag  1914
Val Gly Asn Met Val Asp Pro Lys Tyr Thr Leu Gly Ala Ser Val Asp Lys
```

-continued

```
              335                 340                 345
acg ctt ctc ggc gcg gcc tgagctacgc acgcctggca atggctccgg cgatcgcacg    1972
Thr Leu Leu Gly Ala Ala
350                 355 atggcgccag cctccggtcg agccacctac gcccgcagat cctgccactc gggatggcgg      2032
cggaactgcg tggcaacgta tgaacacagc ggggtgatct tgaagccctc cgcgcgggca      2092
tcggcgatga gggcatccac cagacgcgca gcgatgccgc gcccttcgaa ggccggcggc      2152
acgccgtatg ggtgacgacg aacgggccgt cgccgcggcg ctggtagctc agttccgctt      2212
ccgcaccccc gccgaggcga atgacataac ggcctccgcc cggcccctcc tcgcgctgaa      2272
tctcttggcg agcatcttgg ctggcgtcgt tcatcatgcc tccgtcggtg gtggtgcccc      2332
caccataacg gcgatgctat cccatcagtt catttcgcgc gcctcaagcc cgcgagcgtg      2392
cggaaggcat ctgcgagccc ctccttggac agcggctgca cgaagttgcg aatatagggc      2452
gctgtctccc aggacacgga aacgatgccg tccaccacgg cctcggtctc gacgccgaaa      2512
tcctccagcg cgcgcggcag gccgaggcgg gcgtagaagg ccagcatgtc cgccatgaaa      2572
tcggcgtccc ggccttccgc cagcaattgc accagaagcc cgagggccac ctgttcgcca      2632
tgcagcgccc gcgccaccct cggcaccgtg agaagccgc gcgtgagaga atgggcgatg       2692
gacaggcccc cgctttcgaa ggcgaggccg gagaggagga tggtcgcctc caccacgcgc      2752
tccaccgcct cgtccgccgt cttgcgggcg acggcggcca ccgccgcctc gccatccgcg      2812
cggatggcac ggtagcaggc atcggcgata tgacggcga gcgtggtggg gcgacccttg       2872
aagaaattca gcccgccggc ggcggcgcac tgctctactt caaacttctt ggacagcgca      2932
tcgccgatgc ccgccacgaa gaagcgcgcc ggcgcctgga cgatgacgga tgtatccacc      2992
agcaccgcat cggggttggc atccatcagc cgcacttcgc tcagcacgtg ctcggcggtg      3052
tagaccacca cgaggcggga ggtggggctg tcgttggagg cgatggtcgg cacgatcacg      3112
agcggcgtgc gcagcgcgat gcgcacgccc ttggcggtgt cgatggcctt gccgccgccg      3172
acaccgatca ccacgtcagc gcccgccgcc gcgccgccg cggccagctt gtccatctcc       3232
gccgccgtgc attccccgcc gaaggtggcg aaggtgaccg cctcggcctc cgccagctca      3292
gccttcaggc gcgcccccgag cagatccatc acgatggcgt cggccaccac gaagggccgg    3352
cggcgtgcag gcgcacgagc gcgcccagct caccaagtgc ctcggggccc tggatgtagc      3412
gggccggaga cccgaacgcg cgcacgctca tgcgtcaccc cagtggaaat cgcgcttgcc      3472
gccatccatg cagatcaagg cgccgttgat gaaagccgcc tgcgtggagc agaggaaggc      3532
gacgagcgcc cccacctcct ccggctggca gaagcggccg acgggattct gtccggtgat      3592
caccgcccgc ttctccggcg agaaggtcga tgaaatcggt ggccacatag ccgggcgatg      3652
gcgttcacgg tgatgccgtc cgcccccacc tccttcgcca ccgtgcgggt gaagccgagc      3712
acgccggcct tggccgccga ataattcgcg acgcctggcc ggccgccgcc ggtgacgttc      3772
atggacgagg tgttgacgat gcggccgaag ccatttgcgc gcatcagtgg aatggcgtgc      3832
ttgctgcaca ggaaggtgct gcgcaggtgg gtggagacga tgatgtcgaa gtcgtcgatc      3892
tccatctccg ccacacgccg cccgagatgg cgcccacccg ccccggcatt gttcacgaga      3952
atgtcgaggc gcccgaaggc gtccgcagca gcactcacga cgccagccgc gcccgcctcg      4012
tcggccacgt cgcccgcgtg ccgccgcctc gtacccagcc tgccgcagct ccttggcgca      4072
gtggcggcgc cctccgcgtc gatgtcgttg atgacgatgc gcgcgccctc ggcggcgagc      4132
cccaacgcct ccgcccggcc gatgccggcg ccgcgccggt gacaagggcg accgcccttt      4192
```

-continued

```
tcaatcccag atccatcttg gtctccgatc agcccttcac cgcgcccgcg ccgagcccct    4252
gaatgaagta ttggctcagc aaggcgaagg cgccgaacag cggcaaagcg atgagggtgg    4312
agccggccat gatctccccc cagcgcagat cgaacgaacc gaccatggag ccagcccca    4372 ccggcacggt cttgttggca tcggagccga tcatgatcag cgcataggtg tagtccgtcc    4432
acgacaggag gaaggagaag atggccaccg tgatgagccc cggcagcgac agcggcagca    4492
ccacccgcag gaaggcgccg agccgtgtgc agccatccac catcgccgcc tcttccagct    4552
cgaacggcat gctcttgaag aagccccaca ggaaccacac gccgagcggc agcgtgaggg    4612
tgagatggga gacgatgacg ctcgccagcg tgtcgcccaa ccccagcttg gcgaagatgg    4672
agaacatggg aatggcgatg agcagcggcg ggaacatgta ggcgtagagc atcgccccca    4732
cgatgagccc cttgccgcgg atgcggtggc gcgtgaccgc ataggcgatc atgatcgaga    4792
acaccatggt caccgccacc gtcaccgccg cagacgatga gggaattc                 4840
```

<210> SEQ ID NO 8
<211> LENGTH: 355
<212> TYPE: PRT
<213> ORGANISM: Xanthobacter flavus
<220> FEATURE:

<400> SEQUENCE: 8

```
Met Ser Arg His Pro Met Ser Arg Gln His Ala Ser Arg Pro Leu Thr Pro Pro
 1               5                  10                  15

Pro Tyr Ser Pro Pro Asp Pro Ala Trp Leu Glu Gly Ser Ile Met Ala Ala Arg
        20                  25                  30                  35

Gly Glu Ala Lys Gly Arg Ala Gly Glu Arg Tyr Glu Ile Thr Glu Ala Ser Gln
        40                  45                  50

Gly Lys Tyr His Tyr Val Tyr Gly Pro Tyr Ala Thr Pro Val Leu Arg Val Asp
55                  60                  65                  70

Pro Gly Ala Val Val Ser Ala Glu Thr His Asp Ala Met Glu Gly Gln Ile Lys
            75                  80                  85                  90

Ser Glu Ser Asp Lys Pro Ser Glu Ile Leu Asn Phe Pro Phe Leu Asn Pro Gln
                95                 100                 105

Asn Gly Pro Ile Phe Val Asn Gly Ala Glu Lys Gly Asp Cys Leu Ala Val Tyr
        110                 115                 120                 125

Ile His Asp Ile Val Pro Arg Gly Pro Gln Pro Ile Gly Thr Thr Cys Ile Met
                    130                 135                 140

Pro Glu Phe Gly Gly Leu Val Gly Thr Gly Asp Thr Ala Ile Leu Asn Ala Pro
145                 150                 155                 160

Leu Pro Glu Ile Val Lys Lys Leu His Val Asp Pro Ala Thr Gly Val Arg Trp
                165                 170                 175                 180

Asn Glu Arg Ile Ser Leu Pro Tyr Gln Pro Phe Ile Gly Thr Ile Gly Thr Ala
                    185                 190                 195

Pro Glu Ile Glu Ala Ile Ser Ser Leu Val Pro Asp Tyr Tyr Gly Gly Asn Met
        200                 205                 210                 215

Asp Leu Pro Asp Val Ala Pro Gly Ala Val Ile Tyr Leu Pro Val His Ala Pro
                220                 225                 230

Gly Ala Leu Leu Tyr Leu Gly Asp Cys His Ala Ala Gln Gly Asp Gly Glu Leu
235                 240                 245                 250

Cys Gly Phe Ala Ile Glu His Pro Thr Val Thr Val Gln Ile Asp Leu Ile
        255                 260                 265                 270

Lys Gly Trp Asn Phe Arg Trp Pro Arg Leu Glu Thr His Asp Arg Ile Met Thr
                275                 280                 285
```

-continued

```
Ile Gly Ser Gly Arg Pro Met Glu Asp Ala Ala Arg Ile Ala Tyr Arg Glu Leu
    290                 295                 300                 305

Val Arg Trp Met Ala Ala Asp Tyr Gly Tyr Asp Glu Leu Glu Ala Tyr Met Leu
            310                 315                 320

Leu Thr Gln Ala Gly His Leu Arg Val Gly Asn Met Val Asp Pro Lys Tyr Thr
325                 330                 335                 340

Leu Gly Ala Ser Val Asp Lys Thr Leu Leu Gly Ala Ala
            345                 350                 355

<210> SEQ ID NO 9
<211> LENGTH: 56
<212> TYPE: DNA
<213> ORGANISM: Artificial Sequence
<220> FEATURE:
<223> OTHER INFORMATION: Description of Artificial Sequence Synthetic
      DNA

<400> SEQUENCE: 9
cgccagaagc tttaaggagg aatagcccat gtcccggcat cccatgtccc ggcagc        56

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence Synthetic
      DNA

<400> SEQUENCE: 10
taggtgtcta gaccggaggc tgcc                                            24
```